United States Patent [19]

Bienkowski et al.

[11] 4,147,513

[45] Apr. 3, 1979

[54] METHOD AND APPARATUS FOR MEASURING THE $O_2$ CONTENT OF A GAS

[75] Inventors: Joseph V. Bienkowski; Donald J. Romime; Donald C. Davis, all of Fostoria, Ohio

[73] Assignee: Bendix Autolite Corporation, Fostoria, Ohio

[21] Appl. No.: 836,335

[22] Filed: Sep. 26, 1977

[51] Int. Cl.² ..................... G01N 27/04; G01R 27/02
[52] U.S. Cl. .................................. 23/232 E; 60/276; 73/23; 324/71 R; 338/34; 422/98
[58] Field of Search .... 23/232 E, 254 E, 255 E (U.S. only); 73/23 (U.S. only), 27 R (U.S. only); 338/34; 60/276; 324/65 R (U.S. only), 71 R (U.S. only)

[56] References Cited

U.S. PATENT DOCUMENTS

| | | | |
|---|---|---|---|
| 3,400,054 | 9/1968 | Ruka et al. | 204/195 S X |
| 3,828,749 | 8/1974 | Knapp | 60/276 X |
| 3,915,135 | 10/1975 | Kushida et al. | 123/139 AW X |
| 3,978,006 | 8/1976 | Topp et al. | 204/195 S X |
| 4,001,758 | 1/1977 | Esper et al. | 23/254 E X |
| 4,007,435 | 2/1977 | Tien | 338/34 |

*Primary Examiner*—Joseph Scovronek
*Attorney, Agent, or Firm*—Raymond J. Eifler

[57] ABSTRACT

A method and apparatus for measuring the $O_2$ content in an exhaust gas of an internal combustion engine by exposing two resistors to the exhaust gas of an internal combustion engine. The resistance of both resistors varies as a function of the temperature of the exhaust gas to which it is exposed. However, the resistance of one of the resistors also varies as a function of the oxygen content of the exhaust gas. Therefore, an electrical signal can be obtained which is a function of the $O_2$ content of the exhaust gas, with the temperature effect of the exhaust gas on the resistor being minimized or eliminated.

18 Claims, 6 Drawing Figures

METHOD AND APPARATUS FOR MEASURING THE O₂ CONTENT OF A GAS

CROSS REFERENCE TO RELATED APPLICATIONS

This application, which covers a method and apparatus for measuring the oxygen content of gas, is related to application Ser. No. 836,188 filed Sept. 26, 1977, entitled "Temperature Compensated Oxygen Sensor" which covers only the oxygen sensor.

BACKGROUND OF THE INVENTION

This invention is related to a method and apparatus for sensing the O₂ content of an exhaust gas of an automobile engine. The invention is more particularly related to an improved resistance type oxygen sensor having a titania resistor and a zirconia resistor.

Internal combustion engines, particularly automotive internal combustion engines, have exhaust gases which contain carbon monoxide, nitrogen oxides, and non-oxidized hydrocarbons, i.e., unburned or only partially burned hydrocarbons. All these substances contribute to air pollution. In order to reduce these substances which cause air pollution to a minimum value, it is necessary to clean the exhaust gases from the internal combustion engines as much as possible by effectively removing the largest possible quantity of these substances from the exhaust gases. This means that carbon monoxide and unburned hydrocarbons should be oxidized as completely as possible into their next higher oxidation stage, namely carbon dioxide and water (for the hydrocarbons), and the nitrogen-oxide compound should be converted to elemental nitrogen and oxygen.

Conversion of the noxious components of exhaust gases to non-poisonous compounds like carbon dioxide, nitrogen and water can be obtained by subjecting the exhuast gases to after-burning, i.e., subjecting them to temperatures above about 600° C. while exposing them to catalysts. In order to succeed in this method, however, the composition of the exhaust gases must be so controlled that practically complete conversion of the exhaust gases to the non-poisonous compounds is possible. This means that the relationship of air to fuel is close to the stoichiometric value. As a measure of the stoichiometric value, the air number lambda has been used. At a value of lambda equal to one, the relationship of air to fuel is stoichiometric. If no excess oxygen is present which exceeds the equilibrium of the various possible reactions, lambda is less than one. If, however, lambda is greater than one, excess oxygen is present in the mixture. At lambda equal to one, the gas changes from a reducing to an oxidizing state.

To obtain a value of the air number lambda at approximately one requires that a sensing element be provided which is exposed to the exhaust gases and which determines oxygen content; this sensing element is then connected to a control device which controls the fuel or air supply and provides the correct ratio of fuel and air mixture to the internal combustion engine so that the exhaust gases will have as low a value of noxious components as possible.

Sensing elements which operate on the principle of elemental oxygen concentration and utilizing ion conductive cell electrodes have been used. The principles on which a solid electrolyte sensor operates is explained in great detail in U.S. Pat. No. Re. 28,792, reissued Apr. 27, 1976 (previous U.S. Pat. No. 3,400,054). This patent illustrates a solid electrolyte oxygen sensor which, when one side is exposed to exhaust gases and on the other side exposed to ambient air, provides an electrical signal which is a function of elemental oxygen concentration; both sides of the solid electrolyte are covered at least in part with platinum to form electrodes. The electrolyte is generally stabilized zirconia. Another example of such a sensor may be found in U.S. Pat. No. 3,978,006 entitled "Methods for Producing Oxygen-Sensing Element, Particularly for use with Internal Combustion Engine Exhaust Emission Analysis", issued Aug. —, 1976.

Another type of oxygen sensor is one wherein the electrical resistance of the sensor changes with the amount of oxygen present in the gas. This type of sensor is generally referred to as a resistance type sensor and the principle of operation of such a sensor is explained in U.S. Pat. No. 3,558,280 entitled "Solid-State Oxygen Gage" issued Jan. 22, 1971. The use of a titania resistance type sensor in an engine exhaust control system is also explained in U.S. Pat. No. 3,915,135 entitled "Circuit for Converting a Temperature Dependent Input Signal to a Temperature Independent Output Signal" issued Oct. 28, 1975.

The resistance type (titania) oxygen sensor has certain disadvantages. For instance, the titania sensor must operate over a range from 300° C. to 900° C., but the electrical resistance of the sensor, over the entire range, does not change in a manner that permits a delineation between a lean air-fuel mixture and a rich air-fuel mixture. Specifically, for a lean air-fuel mixture over the range of 300° C. and 900° C., the dc resistance of a titania sensor drops from $3 \times 10^9$ ohms down to about $2 \times 10^4$ ohms, while the dc resistance for a rich air-fuel mixture, over the same range, varies from $3 \times 10^6$ ohms down to about 40 ohms. Therefore, the resistance characteristics for a rich and a lean mixture for the sensor overlap. Accordingly, for any temperature excursion exceeding about 250° C. it is impossible, with an uncompensated titania sensor, to determine whether the air/fuel ratio is rich or lean. Of course, this is undesirable, as it would not be possible to control the air-fuel mixture because the titania type sensor cannot distinguish between a rich air to fuel mixture and a lean air to fuel mixture at temperature excursions above 250° C.

An example of a gas sensor of titania ceramic material which includes a circuit for converting a temperature dependent input signal to a temperature independent output signal and control the air to fuel ratio of an automobile engine is shown in previously mentioned U.S. Pat. No. 3,915,135.

SUMMARY OF THE INVENTION

This invention provides an oxygen sensing system which essentially nullifies the effect of the temperature of the gas on the sensing element.

The invention is a method and apparatus for providing a voltage across a first (1) and second (2) resistor, the resistance of both varying as a function of temperature and the resistance of one (titania) also varying as a function of oxygen, and providing electrical signal (at A and B) which is a function of the ratio of the voltage across the first resistor to a voltage which is a function of the voltage across the both resistors or the second resistor, whereby when the resistors are exposed to the heated gas the electrical signal provided is a function of the oxygen content in the gas.

Accordingly, it is an object of this invention to provide a new method and apparatus for measuring the $O_2$ content of a gas.

It is another object of this invention to provide an oxygen sensing system and method which performs well as temperatures from below 250° C. to above 850° C.

It is another object of this invention to provide a simply constructed oxygen sensing system using inexpensive electronic circuitry.

It is still another object of this invention to provide an oxygen sensing system which will not require adjustment of the electronic circuitry upon installation or upon replacement of the sensor. For example, there is no trimming or matching of the electronic circuitry to the sensor.

It is another object of this invention to improve the performance of an oxygen sensing system and method using a titania type oxygen sensor by minimizing the effect of temperature on such sensors.

Accordingly, this system uses a zirconia chip as a compensation device while other systems, such as that shown in U.S. Pat. No. 3,915,135, previously discussed, uses a platinum wire resistor (or heater) as the temperature compensation device. The zirconia chip in this system has a temperature response very similar to a titania chip; that is an exponential decrease in resistance as a function of increasing temperature. The platinum wire resistor in the foregoing patent has a linear response, i.e. the change in resistance of the platinum wire is directly proportional to the change in temperature. The use of a linear device as the compensation element in the system shown in the patent severely limits the range of temperatures over which that system is operable. See column 6 of U.S. Pat. No. 3,915,135 where it is stated that "the temperature dependency of the resistance value of the titania sensor demonstrates a substantially linear characteristic over the temperature range of interest". Therefore, since the resistance of a titania sensor varies so widely with changes of temperature, it is apparent that the use of a linear element for temperature compensation results in a sensing system that operates over a very narrow range of temperatures. On the other hand, the exponential temperature characteristics of the zirconia element of this system affords excellent temperature compensation from below 250° C. to over 950° C.

The above and other objects and features of the invention will become apparent from the following detailed description taken in conjunction with the accompanying drawings and claims which form a part of this specification.

DETAILED DESCRIPTION OF THE DRAWINGS

Figure 1:
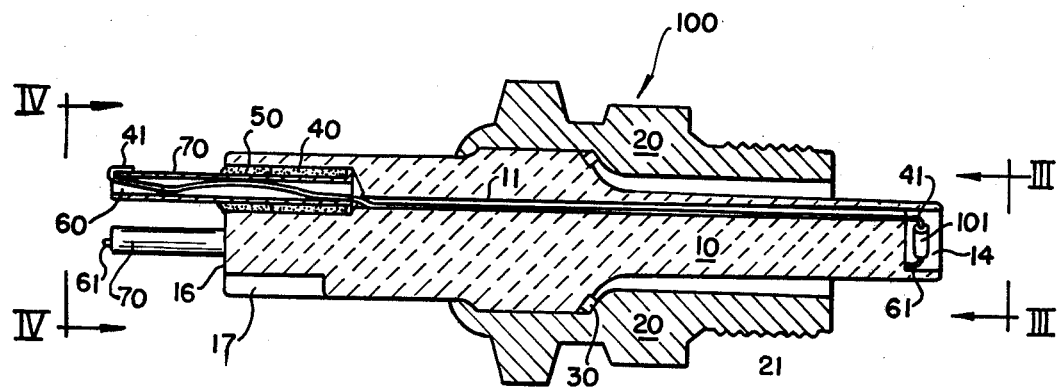
FIG. 1 is a cross sectional view of an oxygen sensor incorporating the principles of this invention.

Referring now to the drawings, FIG. 1 illustrates a cross sectional view of an oxygen sensor 100. The oxygen sensor 100 is comprised of a housing 20 having mounted therein a ceramic insulator 10. The ceramic insulator 10 includes a plurality of passages therethrough for electrical leads. Passageway 11, for instance, allows electrical lead 41 to pass from resistor 101 mounted at the front end, to terminal 70 mounted at the rear end of the insulator 10. The front end of the insulator 10 includes a recessed portion 14 having mounted therein resistor 101, comprised of a material whose resistance varies as a function of the temperature and oxygen content of the gas to which it is exposed. One such material is titania. Leads 41 and 61 extend from the resistor 101 through the ceramic insulator 10 and terminate at terminals 70 to the rear end of the insulator. Each terminal 70 is cemented at 40 and epoxied at 50 to the ceramic insulator 10 while each electrical lead is silver soldered 60 to a terminal 70. The housing 20 includes a plurality of thread 21 which enable the sensors to be attached to similar threads in the exhaust system of an automobile engine. A notch 17 is placed in the rear end of the insulator as a visual indication of the orientation of the electrical leads.

Figure 2:
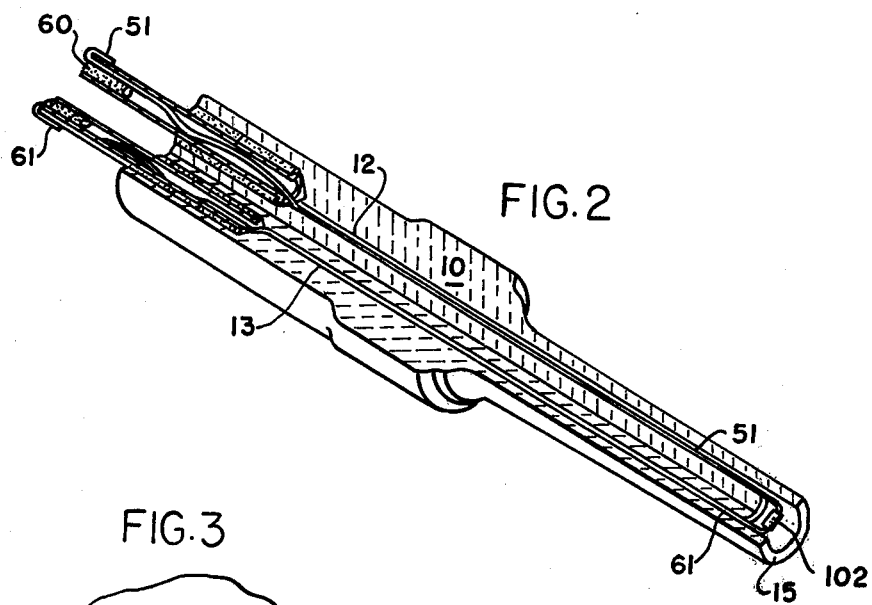
FIG. 2 is another cross sectional area of a portion of the oxygen sensor shown in FIG. 1.

FIG. 2 illustrates another cross sectional view of the insulator 10 of the oxygen sensor 100. Just before the end 15 of the insulator 10 there is mounted in the recess 14 a resistor 102 whose resistance varies as a function of only the temperature to the gas to which it is exposed. Leads 51 and 61 coming from the resistor 102 travel through the passageways 12 and 13 to the terminal 20 at the rear end of the insulator. Resistor 102 is comprised of a material such as zirconia, stabilized by elements such as calcium, barium, strontium, yttrium, lanthanum, scandium, ytterbium and samarium. Calcium stabilized zirconia and yttrium stabilized zirconia are well known and are obtained by adding approximately 0.05 to 0.3% (Mole weight) of yttria $Y_2O_3$ or CaO to zirconia ($ZrO_2$). Other examples of materials that can be substituted for the zirconia are yttrium oxide ($Y_2O_3$), aluminum oxide ($Al_2O_3$), cerium oxide ($CeO_2$), hafnium ($HfO_2$) and thorium ($Th_2O_3$).

Figure 3:
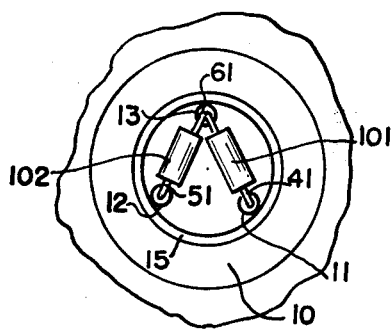
FIG. 3 is a partial front view of the oxygen sensor shown in FIGS. 1 and 2.

FIG. 3 is a front view of the sensor shown in FIGS. 1 and 2 and illustrates the arrangement of the two resistors, 101 and 102, which are exposed to the hot exhaust gases of an internal combustion engine. The forward free end 15 of the insulator 10 surrounds the resistors to protect them from a direct flow of gas across their surfaces. Passageways 11, 12 and 13 in the ceramic insulator 10 return leads 41, 51 and 61 to the terminals at the other end of the sensor, lead 61 being the lead which joins the junction between the titania resistor and the zirconia resistor.

Figure 4:
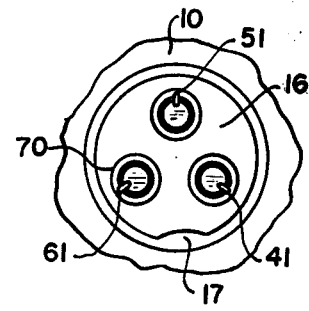
FIG. 4 is a partial end view of the oxygen sensor shown in FIGS. 1 and 2.

FIG. 4 illustrates an end view of the sensor 100 shown in FIGS. 1 and 2 and illustrates the three terminals for receiving and transmitting the voltages to the leads 41, 51 and 61 which, in turn, receive and transmit the voltages across resistors 101 and 102. Cut out portion 17 on the insulator 10 is used to assist in identifying the location of terminals 41, 51 and 61.

Figure 5:
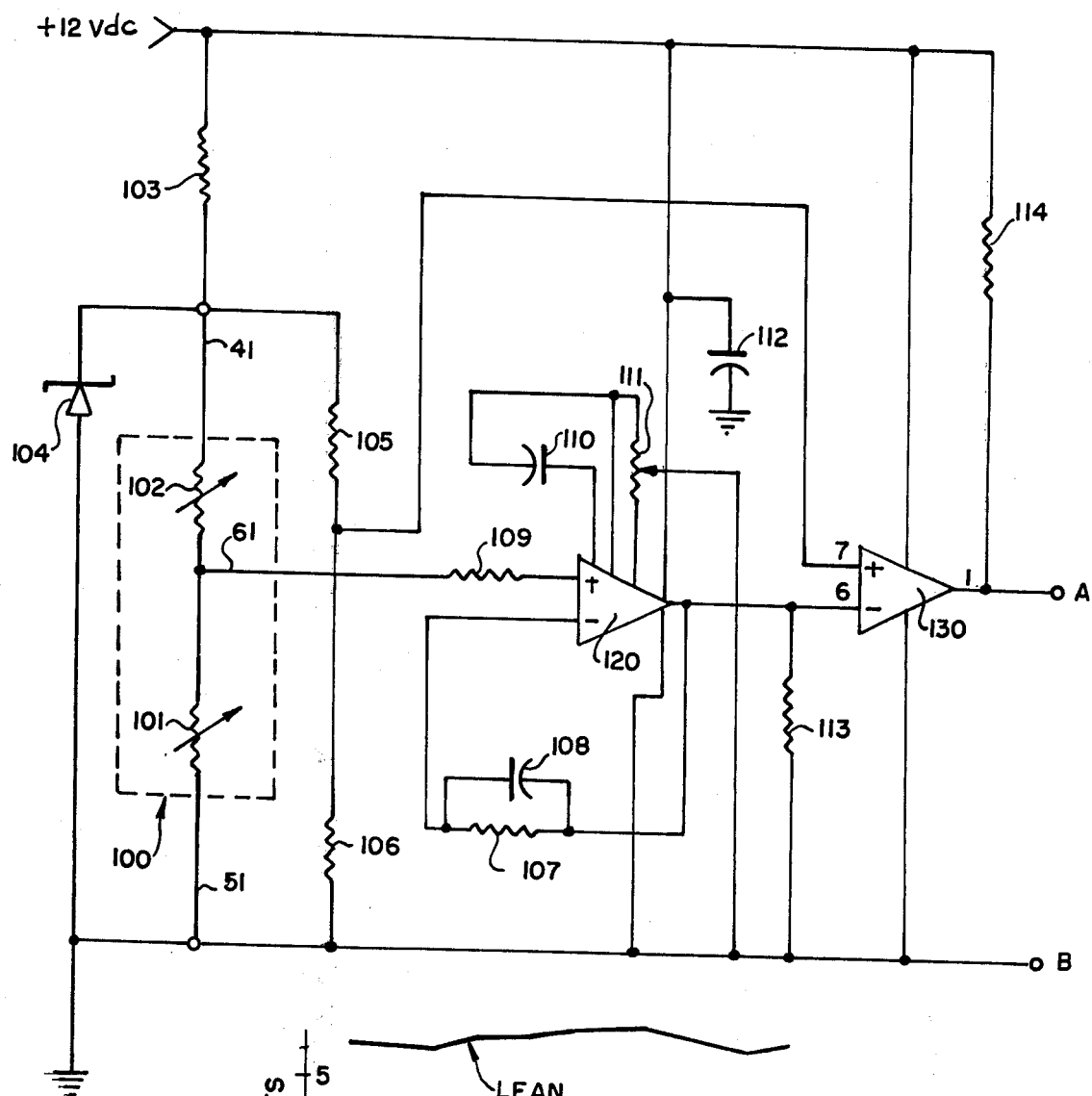
FIG. 5 is a schematic diagram of the electrical circuit used in the method and apparatus of the invention to measure the $O_2$ content in an exhaust gas of an internal combustion engine.

FIG. 5 illustrates the electrical circuitry that incorporates resistors 101 and 102 of sensor 100 and provides an indication, at outputs A and B, of the $O_2$ content of a gas applied to the resistors 101 and 102. The circuit consists generally of a battery (12 volt dc); a voltage regulating network 103, 104; a voltage divider network 105, 106; a temperature compensated titania sensor 101, 102; a buffer amplifier 120; and a comparator 130, which may be of the type that provides a digital output. Zener diode 104 establishes a maximum voltage level across the fixed resistors 105, 106, and variable resistors 101, 102. The zener diode 104 is provided to limit the voltage across resistors 101 and 102 as well as across resistors 105 and 106. With a 12 volt DC input this circuit is designed to provide a signal of greater than 1.5 volts across resistor 101 when the exhaust is lean and a voltage of less than 1.5 volts across resistor 101 when the exhaust gas is rich. Similarly, the values of resistance for resistors 103, 105 and 106 are chosen so that the voltage across resistor 106, which is a voltage signal fed to pin 7 of comparator 130, is about 1.5 volts. The voltage across resistor 101 is transmitted to input pin 6 of the comparator 130 through buffer amplifier 120. When the voltage across resistor 101 is greater than 1.5 volts (the voltage across resistor 106) then the signal to the comparator 130 at pin 6 is greater than the signal at pin 7 and the comparator output is zero. When the voltage across resistor 101 drops to less than 1.5 volts the signal to the comparator 130 at pin 7 is then larger than the voltage at pin 6 and accordingly the comparator puts out a 12 volt signal which is digital. Obviously, to reverse the phase of the comparator output, leads 7 and 6 need merely be switched.

The following is a table identifying the components and their values used in one operable embodiment of the invention:

| Element No. | Description |
| --- | --- |
| 101 | Titania Resistor |
| 102 | Zirconia Resistor |
| 103 | 270 ohms |
| 104 | 6.2 volt Zener |
| 105 | 4.5K Ohms |
| 106 | 1.5K Ohms |
| 107 | 2K Ohms |
| 108 | .1 uf |
| 109 | 10K Ohms |
| 110 | 56 pf |
| 111 | 100K ohms |
| 112 | .01 uf |
| 113 | 1K Ohms |
| 114 | 1K Ohms |
| 120 | RCA CA3130AE or Texas Instruments TL080 |
| 130 | Motorola MC3302P |

Typical examples of the resistance of resistors 101 and 102 at different temperatures are as follows:

for a RICH air to fuel mixture the resistance across the zirconia resistor 102 at 400° C. is $3 \times 10^7$ and at 750° C. 6K Ohms;

for the same air to fuel mixture and temperature range the resistance of the titania resistor is 140K Ohms and 120 ohms respectively;

for a LEAN air to fuel mixutre the resistance of the zirconia resistance at 400° C. is $3 \times 10^7$ Ohms and at 750° C. 6K Ohms; and similarly the resistance of the titania resistor for the same mixture and temperatures is greater than $1 \times 10^9$ Ohms and 280K Ohms respectively.

Accordingly, it follows that the ratio of the titania resistance 101 to the sum of the resistance of both resistors 101 and 102 is quite small at a temperature of 400° C. to 750° C. for a rich mixture (about 0.00467 and 0.0196). However, at a lean air to fuel mixture over a temperature range of 400° C. to 750° C., it follows that the ratio of the resistance of the titania resistor 101 to the total resistance of both resistors 101, 102 increases significantly compared to the same ratio for a rich mixture (about 0.97 and 0.98). Hence the voltage across the titania resistor increases significantly for a lean air mixture to that of a rich air mixture.

Figure 6:
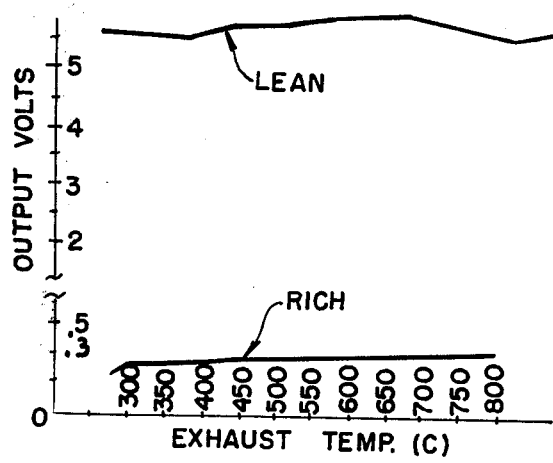
FIG. 6 is a graph illustrating the voltage across the titania resistor as a function of temperature.

FIG. 6 is a graph illustrating the voltage across the titania resistor as a function of the temperature of the resistor. The x axis is in degrees centigrade of the exhaust gas temperature around the resistor. The y axis is the output voltage measured across the titania resistor when operating in the circuit shown in FIG. 5. The lower curve shows the voltage less than 0.3 volts for a rich air to fuel mixture, across the titania resistor for temperatures from about 300° C. to 800° C. Similarly, the voltage for a lean air to fuel mixture, across the titania resistor for the same temperature range is greater than 5 volts. Accordingly, when the voltage is above or below a predetermined value it can be determined from the exhaust gas whether there is a rich or lean mixture of air to fuel. For instance, for a reference voltage of 1.5 volts (voltage across resistor 106), whenever the voltage is above 1.5 volts at the titania resistor 101, the air to fuel ratio is lean and when the voltage across the titania resistor 101 is less than 1.5 volts, the exhaust gas indicates a rich air to fuel ratio going into the engine.

Since the resistance of the zirconia resistor 102 changes resistance with temperature in about the same manner as does the resistance of the titania resistor, the voltage divided between the two resistors will remain substantially the same unless there is a change in the resistance of the titania resistor as a result of the $O_2$ content. Therefore, since the resistance of the zirconia resistor varies only with the temperature to which it is exposed while the resistance of the titania resistor varies similarly as a function of the temperature and also of the $O_2$ content the voltage divided between resistor 101 and 102 can be considered as temperature compensated and therefore the voltage across titania resistor 101 would be indicative of the oxygen content of the gas with the effect of temperature being minimized or eliminated completely.

OPERATION

In operation, the comparator 130 compares the voltage signal across titania resistor 101 (supplied through input pin 6) to the voltage across resistor 106 (supplied through input pin 7), and provides output signals when the signal at input 7 is greater and less than the signal at input 6.

Since the voltage across titania resistor 101 is a function of the oxygen content in a gas to which it is exposed, the signal provided at outputs A and B be a function of the $O_2$ content in such gas.

When a voltage of 12 volts is supplied to the circuit in FIG. 5 and resistors 101 and 102 are inserted in the exhaust gas from an internal combustion engine, the output at A and B of the circuit will provide an indication of the oxygen content in the exhaust gas and therefore can be useful in determining and adjusting the air to fuel ratio entering such engine.

When the resistors 101 and 102 are exposed to an exhaust gas, the temperature of exhaust gas will change the resistance of resistors 101 and 102. However, since both resistors have been chosen to have resistances which vary about the same percentage with temperature the voltage divided across both resistances will remain about the same. However, when the oxygen content of the exhaust gas decreases, the resistance of titania resistor 101 will decrease. This means that when there is a rich (more fuel and less air than when mixture is lean) air to fuel mixture (see FIG. 6) going into the engine, the $O_2$ content in the exhaust gas is less than it would be when a lean air to fuel mixture goes into the engine.

Conversely, when the titania resistor is exposed to an exhaust gas having more oxygen (a lean air to fuel mixture) the voltage across titania resistor increases to greater than 1.5 volts (see FIG. 6).

The voltage across the titania resistor is transmitted through buffer amplifier 120 to input terminal 6 of comparator 130. Comparator 130 then compares this voltage signal to the voltage signal across resistor 106 (which remains the same). When the voltage at input pin 7 is greater than a voltage at input pin 6, the comparator 130 puts out a 12 volt signal indicating less fuel should be supplied to the air/fuel mixture going into the engine. When the voltage at input pin 7 is less than the voltage at input pin 6 the comparator 130 puts out a signal (zero volts) indicating that more fuel should be supplied to the air/fuel mixture going into the engine.

While a preferred embodiment of this invention has been disclosed, it will be apparent to those skilled in the art that changes may be made to the invention as set forth in the appended claims, and, in some cases, certain features of the invention may be used to advantage without corresponding use of other features. For example, zener diode 104 may or may not be used. Further, while only titania and zirconia have been suggested as the material to be used for the resistors, other materials may be used so long as the resistance to temperature characteristics of both materials are substantially similar or change in equal proportions, and so long as one of the materials has a resistance which varies also with the $O_2$ content to the gas to which it is exposed. Accordingly, it is intended that the illustrative and descriptive materials herein be used to illustrate the principles of the invention and not to limit the scope thereof.

Having described the invention what is claimed is:

1. A method for measuring the oxygen content in an exhaust gas of an internal combustion engine, the method comprising:

electrically connecting a first resistor comprised of titania in series with a second resistor comprised of stabilized zirconia, said second resistor having about the same resistance-temperature characteristics as said first resistor over a predetermined temperature range of said gas;

applying a potential across the resistors;

exposing said resistors to the exhaust gas of an internal combustion engine; and obtaining, from said resistors, an electrical signal which is a function to the ratio of the voltage across the first resistor to the voltage across the second resistor.

2. An electrochemical oxygen sensing apparatus for determining the oxygen content in the exhaust gas of an internal combustion engine, said sensing apparatus comprising:

a first resistor comprised of a titania material;

a second resistor comprised of stabilized zirconia material, said second resistor having about the same resistance-temperature characteristics as said first resistor over a predetermined temperature range of said gas;

means for electrically connecting said titania resistor in series with said stabilized zirconia resistor;

means for applying a voltage across said series connection of said titania resistor and stabilized zirconia resistor; and means for obtaining an electrical signal which is a function of the ratio of the voltage across the first resistor to the voltage across the second resistor, whereby when a voltage is applied to said resistors and said resistors are exposed to the exhaust gas of an internal combustion engine, the electrical signal is related to the oxygen content in the exhaust gas.

3. The sensing apparatus as recited in claim 2 including a zener diode connected across the series combination of both resistors.

4. An electrochemical oxygen sensing apparatus for determining the oxygen content in a gas, said sensing element comprising:

a first resistor, the resistance of which varies as a function of both the temperature of said gas to which it is exposed and the oxygen content of said gas;

a second resistor, the resistance of which varies as a function of only the temperature of said gas to which it is exposed, said second resistor having about the same resistance-temperature characteristics as said first resistor over a predetermined temperature range of said gas;

means for electrically connecting said first resistor in series with said second resistor;

means for applying a voltage across said first resistor in series with said second resistor;

means for applying a voltage across said first and second resistors; and means for obtaining, from said resistors, an electrical signal, which is a function of the ratio of the voltage across the first resistor to the voltage across both resistors, whereby when said resistors are exposed to a heated gas said electrical signal is a function of the oxygen content in said gas.

5. An electrochemical oxygen sensing element as recited in claim 4 wherein the first resistor is comprised of titania.

6. An electrochemical oxygen sensing element as recited in claim 5 wherein the second resistor is comprised of stabilized zirconia.

7. An electrochemical oxygen sensing apparatus for determining the oxygen content in a gas, said sensing element comprising:

a first resistor, the resistance of which varies as a function of both the temperature of said gas to which it is exposed and the oxygen content of said exhaust gas;

a second resistor, the resistor of which varies as a function of only the temperature of said gas to which it is exposed, said second resistor having about the same resistance-temperature characteristics as said first resistor over a predetermined temperature range of said gas;

means for electrically connecting said first resistor in series with said second resistor;

means for applying a voltage across said first and second resistors;

means for measuring the voltage across one of said resistors;

means for obtaining, from said resistors, a reference voltage which is a function of the voltage across both resistors; and means for comparing the voltage measured across said one of said resistors to said reference voltage and providing a first output signal when the voltage across said one of said resistors is greater than said reference voltage and providing a second output signal when the voltage across said one of said resistors is less than said reference voltage.

8. An electrochemical oxygen sensing element as recited in claim 7 herein said first resistor is comprised of titania and said second resistor is comprised of stabilized zirconia.

9. An electrochemical oxygen sensing element as recited in claim 7 including means for maintaining the voltage applied across said first and second resistors at a constant value.

10. An electrochemical oxygen sensing element as recited in claim 8 including means for maintaining the voltage applied across said first and second resistors at a constant value.

11. An electrochemical oxygen sensing element as recited in claim 7 wherein said first resistor is comprised of titania.

12. An electrochemical oxygen sensing element as recited in claim 9 where in said first resistor is comprised of titania.

13. A method for providing an electrical signal which is related to the $O_2$ content of a gas, the method comprising:
electrically connecting a first resistor comprised of titania in series with a second resistor comprised of stabilized zirconia material, said second resistor having about the same resistance-temperature characteristics as said first resistor over a predetermined temperature range of said gas;
applying a potential across the resistors;
exposing said resistors to a gas;
obtaining a first electrical output across said titania resistor as an indication of the $O_2$ content of the gas;
obtaining a second electrical output which is a function of the voltage across both of said resistors; and
comparing said first electrical output to said second electrical output and obtaining an output signal which is a function of said first and second output signals.

14. The method for measuring the $O_2$ content in a gas as recited in claim 13 wherein the step of connecting said resistors includes connecting said resistors in series to each other.

15. A method for measuring the $O_2$ content of a gas, method comprising:
electrically connecting in series a first resistor made of titania, the resistance of which varies as a function of both the temperature of the gas to which it is exposed and the oxygen content of said gas, to a second resistor, the resistance of which varies as a function of only the temperature of the gas to which is it exposed, said resistor having about the same resistance-temperature characteristics as said first resistor over a predetermined temperature range of said gas;
applying a voltage across said series connected resistors;
exposing said resistors to a gas;
obtaining a first electrical signal which is a function of the voltage across said titania resistor;
obtaining a second electrical signal which is a function of the voltage applied across both of said resistors; and
comparing said first electrical signal to said second electrical signal and obtaining an output signal which is a function of said first and second electrical signals.

16. A method for measuring the $O_2$ content of a gas as described in claim 15 wherein the step of obtaining a second electrical signal comprises:
providing a voltage divider network across said first and second resistors; and
obtaining the second electrical signal from said voltage divider network.

17. The method recited in claim 15 including the step of maintaining the voltage applied across said series connected resistors at a constant value.

18. The method recited in claim 16 including the step of maintaining the voltage applied across said series connected resistors at a constant value.

* * * * *